United States Patent [19]

Ning

[11] Patent Number: 5,666,222

[45] Date of Patent: Sep. 9, 1997

[54] OPTICAL VIEWING DEVICE

[75] Inventor: Xiaohui Ning, Northboro, Mass.

[73] Assignee: United States Surgical Corporation, Norwalk, Conn.

[21] Appl. No.: 389,473

[22] Filed: Feb. 16, 1995

Related U.S. Application Data

[62] Division of Ser. No. 944,212, Sep. 11, 1992, Pat. No. 5,416,634.

[51] Int. Cl.[6] .......................... G02B 23/00; G02B 23/24
[52] U.S. Cl. .................................. 359/435; 359/434
[58] Field of Search .......................... 359/362, 434–435, 359/643–646; 385/117–119; 600/139, 184, 172, 120, 129, 157, 160–167; 128/4–6

[56] References Cited

U.S. PATENT DOCUMENTS

| | | | |
|---|---|---|---|
| 2,245,257 | 6/1941 | Crumrine | 359/819 |
| 2,266,169 | 12/1941 | Crumrine | 249/95 |
| 2,304,984 | 12/1942 | Wood | 264/275 |
| 2,341,364 | 12/1944 | Crumrine | 359/819 |
| 2,388,893 | 11/1945 | Wood | 359/819 |
| 2,482,971 | 9/1949 | Golson | 600/184 |
| 3,089,484 | 5/1963 | Hett | 600/139 |
| 3,257,902 | 6/1966 | Hopkins | 359/435 |
| 3,294,085 | 12/1966 | Wallace | 369/263 |
| 3,297,022 | 1/1967 | Wallace | 600/172 |
| 3,414,344 | 12/1968 | Mukollmar | 359/435 |
| 3,484,148 | 12/1969 | Gotoh | 359/399 |
| 3,498,286 | 3/1970 | Plyani et al. | 128/634 |
| 3,556,085 | 1/1971 | Takahashi | 600/129 |
| 3,677,262 | 7/1972 | Zukowski | 600/120 |
| 3,807,836 | 4/1974 | Baker | 359/775 |
| 3,888,568 | 6/1975 | Norris et al. | 359/823 |
| 3,903,877 | 9/1975 | Terada | 600/157 |
| 3,941,121 | 3/1976 | Olinger et al. | 600/167 |
| 4,025,155 | 5/1977 | Imai | 359/435 |

(List continued on next page.)

FOREIGN PATENT DOCUMENTS

| | | |
|---|---|---|
| 0100517 | 2/1984 | European Pat. Off. |
| 3004089 | 11/1980 | Germany. |

(List continued on next page.)

OTHER PUBLICATIONS

Thomas Aquilina, David Richards and Harvey Pollicove, Technolgoy Trends, Sep. 1968, Photonic Spectras.

Harvey Pollicove and Thomas Aquilina, Injection Mounting, Dec. 1987, Photonics Spectra.

(List continued on next page.)

*Primary Examiner*—Thong Nguyen

[57] ABSTRACT

A low cost optical viewing device for viewing a remote location comprises three sections of an objective lens, relay lens and eye piece. However, in contrast to prior art optical viewing devices, all three sections of the present invention are free of conventional and relatively expensive glass rods. The preclusion of the glass rods leads to an overall lower cost (e.g., disposable) optical viewing device (e.g, borescope and endoscope). In addition, the optical viewing device of the present invention achieves lower cost by the use of a combination of molded plastic lenses and glass lenses. In accordance with still another important feature of this invention, the method of illuminating the remote location to be viewed is accomplished by using low cost plastic optical fibers which are twisted so that the field of illumination is increased and may be tailored to match (or be no less than) the size of the field of view of the optical viewing device. Still another significant feature of the present invention is its low weight as compared to prior art devices. This low weight is obtained both through the use of the combination of lightweight plastic lenses and glass lenses as well as by the fact that the lenses are separated by an air space (as opposed to heavy glass rods). This light weight feature of the present invention leads to ease of manipulation by the end user.

12 Claims, 4 Drawing Sheets

U.S. PATENT DOCUMENTS

| | | | |
|---|---|---|---|
| 4,036,218 | 7/1977 | Yamashita et al. | 600/160 |
| 4,076,018 | 2/1978 | Heckle | 600/168 |
| 4,146,019 | 3/1979 | Bass et al. | 600/108 |
| 4,148,550 | 4/1979 | MacAnally | 359/435 |
| 4,148,551 | 4/1979 | MacAnally | 359/435 |
| 4,157,216 | 6/1979 | Plummer | 354/62 |
| 4,159,546 | 7/1979 | Shearing | 623/6 |
| 4,217,891 | 8/1980 | Carson | 600/162 |
| 4,272,156 | 6/1981 | Ishibashi et al. | 385/117 |
| 4,273,110 | 6/1981 | Groux | 600/156 |
| 4,281,646 | 8/1981 | Kinoshita | 600/157 |
| 4,319,563 | 3/1982 | Kubota | 600/129 |
| 4,392,485 | 7/1983 | Hoogland | 600/153 |
| 4,545,652 | 10/1985 | Hoogland | 359/715 |
| 4,557,567 | 12/1985 | Azumi et al. | 359/683 |
| 4,569,335 | 2/1986 | Tsuno | 600/158 |
| 4,574,783 | 3/1986 | Kazuhrio et al. | 600/112 |
| 4,575,195 | 3/1986 | Hoogland | 359/716 |
| 4,608,966 | 9/1986 | Hoogland | 600/161 |
| 4,664,486 | 5/1987 | Landre et al. | 359/380 |
| 4,667,655 | 5/1987 | Ogui et al. | 600/132 |
| 4,667,656 | 5/1987 | Yabe | 600/109 |
| 4,676,606 | 6/1987 | Takahashi | 359/754 |
| 4,693,568 | 9/1987 | Takahashi | 359/772 |
| 4,704,007 | 11/1987 | Landre et al. | 359/380 |
| 4,732,448 | 3/1988 | Goldenberg | 385/33 |
| 4,736,733 | 4/1988 | Adair | 600/109 |
| 4,741,326 | 5/1988 | Sidall et al. | 600/123 |
| 4,765,313 | 8/1988 | Kamakura | 600/167 |
| 4,770,163 | 9/1988 | Ono et al. | 600/130 |
| 4,771,766 | 9/1988 | Aoshino et al. | 600/155 |
| 4,778,247 | 10/1988 | Carpenter | 385/117 |
| 4,784,118 | 11/1988 | Fantone et al. | 600/160 |
| 4,802,460 | 2/1989 | Ohkuna et al. | 600/177 |
| 4,805,598 | 2/1989 | Ueda | 600/169 |
| 4,815,816 | 3/1989 | Schneider | 385/116 |
| 4,822,154 | 4/1989 | Oxford et al. | 359/367 |
| 4,838,246 | 6/1989 | Hahn et al. | 600/108 |
| 4,854,302 | 8/1989 | Allred, III | 600/109 |
| 4,869,238 | 9/1989 | Opie et al. | 600/109 |
| 4,878,485 | 11/1989 | Adair | 600/122 |
| 4,919,112 | 4/1990 | Siegmund | 600/136 |
| 4,919,113 | 4/1990 | Sakimota et al. | 600/155 |
| 4,946,267 | 8/1990 | Hoogland | 359/737 |
| 4,964,710 | 10/1990 | Leiner | 600/162 |
| 4,980,763 | 12/1990 | Lig | 348/67 |
| 4,986,622 | 1/1991 | Martinez | 385/16 |
| 4,988,172 | 1/1991 | Kanamori et al. | 358/328 |
| 4,993,817 | 2/1991 | Hoogland | 359/708 |
| 5,046,816 | 9/1991 | Lehmann et al. | 385/117 |
| 5,059,009 | 10/1991 | McKinely | 359/435 |
| 5,412,504 | 5/1995 | Leiner et al. | 359/434 |
| 5,416,634 | 5/1995 | Niny | 359/435 |
| 5,461,509 | 10/1995 | Canzek | 359/434 |

FOREIGN PATENT DOCUMENTS

| | | | |
|---|---|---|---|
| 3220350 | 10/1983 | Germany. | |
| 3534210 | 3/1986 | Germany. | |
| 3535028 | 4/1986 | Germany. | |
| 62-181888 | 7/1987 | Japan. | |
| 2129613 | 9/1988 | Japan. | |
| 54422 | 1/1977 | U.S.S.R. | |
| 683721 | 9/1979 | U.S.S.R. | |
| 686725 | 9/1979 | U.S.S.R. | |
| 1068866 | 1/1984 | U.S.S.R. | 359/819 |
| 1173980 | 8/1985 | U.S.S.R. | |
| 8807218 | 9/1988 | WIPO. | |
| 9104703 | 4/1991 | WIPO. | |

OTHER PUBLICATIONS

John D. Lytle, Specifying Glass and Plastic Optics What's The Difference?, 1979 SPIE vol. 181 Contemporary Optical Systems & Components Specifications.

Harold H. Hopkins, Optical Principles of the Endoscopy, 1976.

Patent Abstract of Japan Publication No. JP62279309.

Patent Abstract of Japan Publication No. JP4204901.

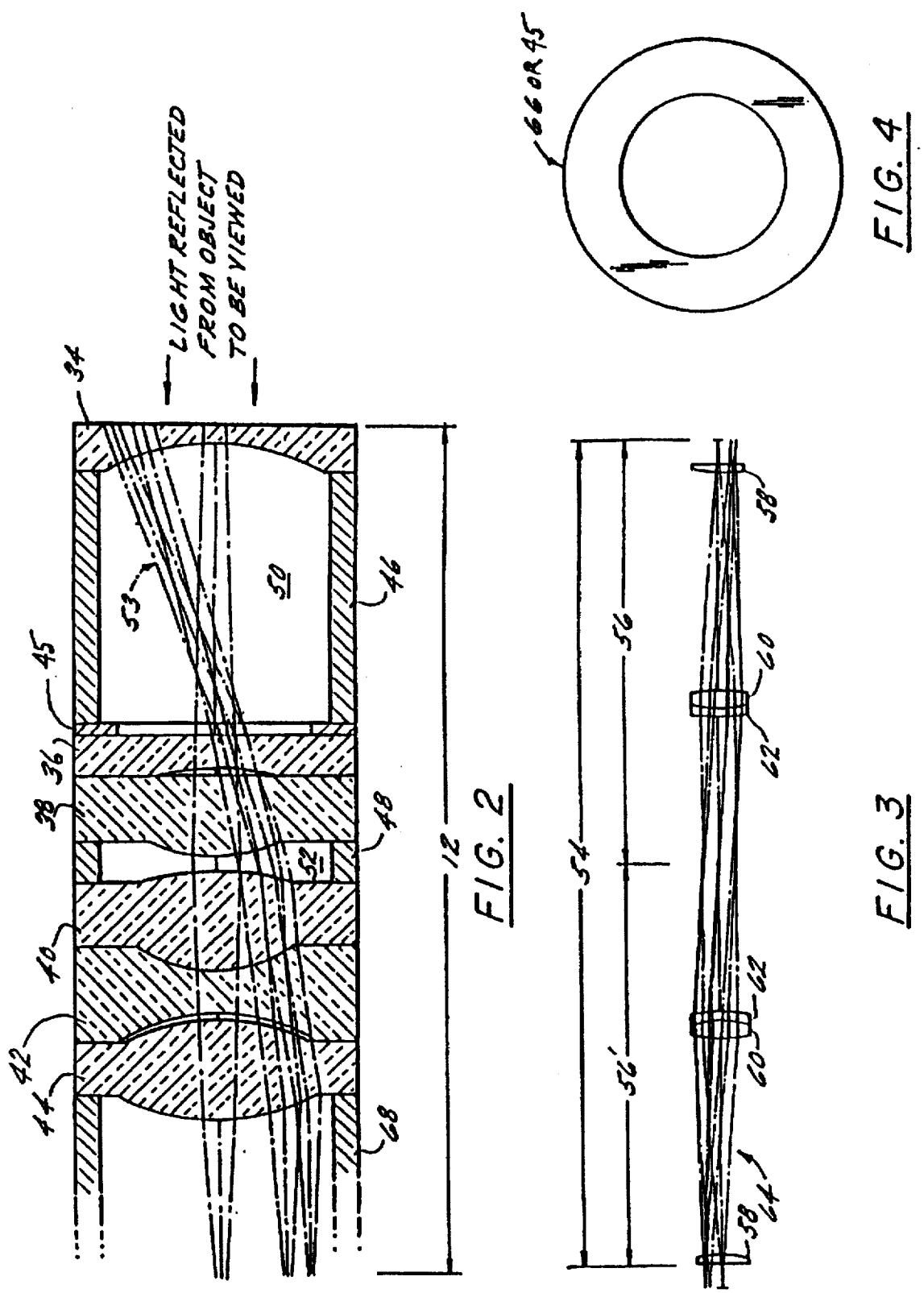

OPTICAL VIEWING DEVICE

This is a divisional of U.S. application Ser. No. 07/944,212 filed Sep. 11, 1992, now U.S. Pat. No. 5,416,634.

BACKGROUND OF THE INVENTION

This invention relates generally to optical viewing devices. More particularly, this invention relates to an optical viewing device for viewing remote locations which are difficult or impossible to directly access.

Optical viewing devices of the type described herein are well known and used in a variety of applications. For example, such devices are configured as borescopes and used to view or inspect the interior of remote cavities such as engine cylinders and the like. Borescopes thus find extensive utility in the automotive and aerospace industries. In the medical field, such optical viewing devices are configured as endoscopes or laparoscopes. Endoscopes (or laparoscopes) are well known medical instruments which are used to visualize the interior of a body cavity or hollow organ. Endoscopes are used in a variety of operative procedures including laparoscopic surgery where endoscopes are used to visually examine the peritoneal cavity.

Typical prior art optical viewing devices (e.g., borescopes and endoscopes) comprise three main sections including an objective lens followed by a relay lens followed by an eye piece. The relay lens section functions to transmit the image rays obtained by the objective lens along a preselected distance to the eye piece. The relay lens may consist of either a coherent fiber optical bundle or a series of lenses. When the relay lens section is comprised of a series of lenses, the lens series traditionally includes repeated units (e.g., three) with each unit comprising a symmetric arrangement of glass rods and lens groupings. Thus, in a prior art device having three relay sections, a total of six glass rods and associated lens groupings were required. These glass rods are used to preclude or lessen divergence of the image rays as they travel through the optical viewing device. Such glass rods must be of a high optical quality and therefore the glass rods lead to a relatively high manufacturing cost for each optical viewing device. Moreoever, in certain prior art viewing devices, the objective lens and eye piece sections also contain glass rods leading to even higher manufacturing costs.

Illumination in the remote location to be viewed is required. A preferred method of transmitting illumination light is to use a bundle of optical fibers surrounding the outer circumference of the optical viewing device. These fibers are generally glass. The field of illumination should be of a size no less than the field of view (FOV) of the optical viewing device. Typically, the FOV may range between 30 to 75 degrees.

Presently, there is a need for low cost and/or disposable optical viewing devices such as borescopes and endoscopes. One method of reducing costs would be to remove the relatively expensive glass rods. However, it has been believed by those skilled in the art that removal of the multiple glass rods sacrifices optical performance in several ways. For example, under certain optical conditions, removal of the glass rods reduces the light gathering ability of the optical viewing device which leads to an overall dimmer edge to the image obtained by the optical viewing device. Also, the length of the optical viewing device must be reduced which in some procedures (e.g., surgical), may be highly undesirable. Thus, it has heretofore been believed that removal of the glass rods from the relay lens section was not a practical or desirable method of producing a lower cost optical viewing device.

The prior art has addressed this problem in U.S. patent application Ser. No. 838,602 filed Feb. 19, 1992 assigned to the assignee hereof and incorporated herein by reference. In U.S. Ser. No. 838,602 a low cost optical viewing device is provided which comprises the traditional three sections of an objective lens, relay lens and eye piece. However, in contrast to the above prior art optical viewing devices, all three sections of the present invention are free of the relatively expensive glass rods. The inventor herein has discovered that deletion of the intermediate glass rods will not sacrifice optical performance. The preclusion of the glass rods in the relay lens section leads to an overall lower cost optical viewing device (e.g., borescope and endoscope).

In addition, the optical viewing device of U.S. Ser. No. 838,602 achieves lower cost by the use of molded plastic lenses rather than the more expensive glass lenses. The method of illuminating the remote location to be viewed in U.S. Ser. No. 838,602 is accomplished by using the low cost plastic optical fibers. However, because plastic optical fibers have a relatively small field of illumination, it has been discovered that by twisting the fibers (e.g., 15 degrees), the field of illumination is increased and may be tailored to match (or be no less than) the size of the field of view of the optical viewing device.

However, the use of molded plastic lenses results in birefringence being introduced into the light. The molded plastic lenses do not have a homogeneous refractive index, this problem is inherent with injection molded plastic lenses. The nonhomogeneous refractive index of the plastic lenses is the cause of the birefringence. This problem results in blurred and/or otherwise distorted images at the eyepiece.

SUMMARY OF THE INVENTION

The above-discussed and other problems and deficiencies of the prior art are overcome or alleviated by the low cost and/or disposable optical viewing device of the present invention. In accordance with the present invention, a low cost optical viewing device is provided which comprises the traditional three sections of an objective lens, relay lens and eye piece. However, in contrast to prior art optical viewing devices, all three sections of the present invention are free of the relatively expensive glass rods. The inventor herein has discovered that deletion of the intermediate glass rods will not sacrifice optical performance. For example, under certain optical conditions, the optical viewing device of this invention will not (1) reduce light gathering; or (2) sacrifice vignetting; or (3) lead to an undesirably reduced length. This discovery leads to an optical viewing device which is relatively low cost, easy to manufacture and therefore disposable. Hence, it will be appreciated that the preclusion of the glass rods in the relay lens section leads to an overall lower cost optical viewing device (e.g, borescope and endoscope).

In addition, the optical viewing device of the present invention achieves lower cost by the use of a combination of molded plastic lenses and glass lenses. The glass lenses are used at selected locations where the birefringence induced by a molded plastic lens is not acceptable. It is preferred in the present invention that the use of glass lenses be minimized.

In accordance with still another important feature of this invention, the method of illuminating the remote location to be viewed is accomplished by using low cost plastic optical fibers. However, because plastic optical fibers have a relatively small field of illumination, it has been discovered that by twisting the fibers (e.g., 15 degrees), the field of illumination is increased and may be tailored to match (or be no less than) the size of the field of view of the optical viewing device.

Still another significant feature of the present invention is its low weight as compared to prior art devices. This low weight is obtained both through the use of a combination of lightweight plastic lenses and glass lenses as well as by the fact that the lenses are separated by an air space (as opposed to heavy glass rods). This light weight feature of the present invention leads to ease of manipulation by the end user.

The above-discussed and other features and advantages of the present invention will be appreciated and understood by those of ordinary skill in the art from the following detailed discussion and drawings.

BRIEF DESCRIPTION OF THE DRAWINGS

Referring now to the drawings, wherein like elements are numbered alike in the several FIGURES:

FIG. 2 is an enlarged cross-sectional elevation view of the objective lens section of the optical viewing device of FIG. 1;

FIG. 3 is an enlarged cross-sectional elevation view of one of three repeating units which comprise the relay lens section of the optical viewing device of FIG. 1;

FIG. 4 is a front elevation view of an aperture stop used in the relay lens section of FIG. 3;

DESCRIPTION OF THE PREFERRED EMBODIMENT

Figure 1:
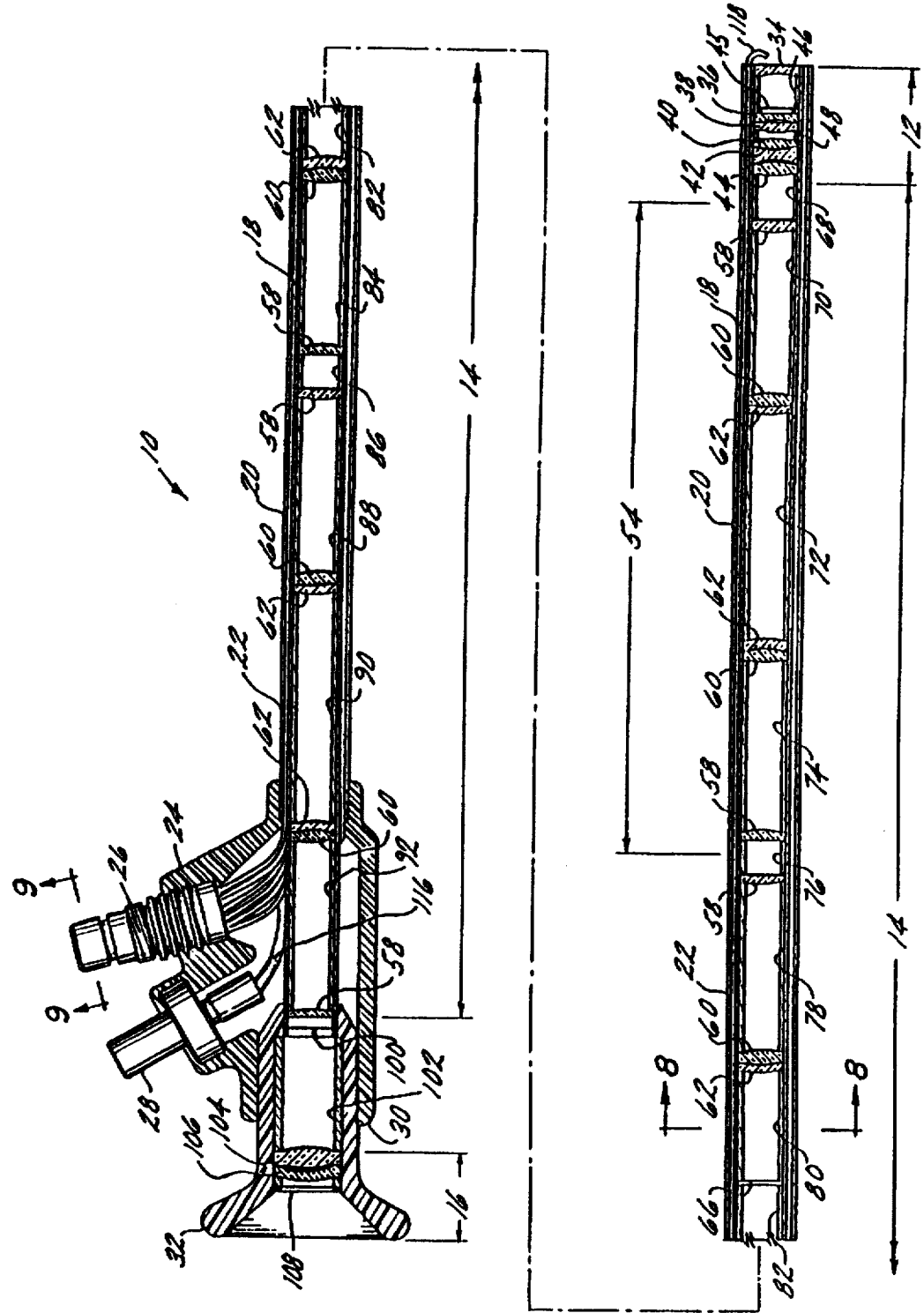
FIG. 1 is a side elevation view, partly in cross-section, of an optical viewing device in accordance with the present invention.
Figure 8:
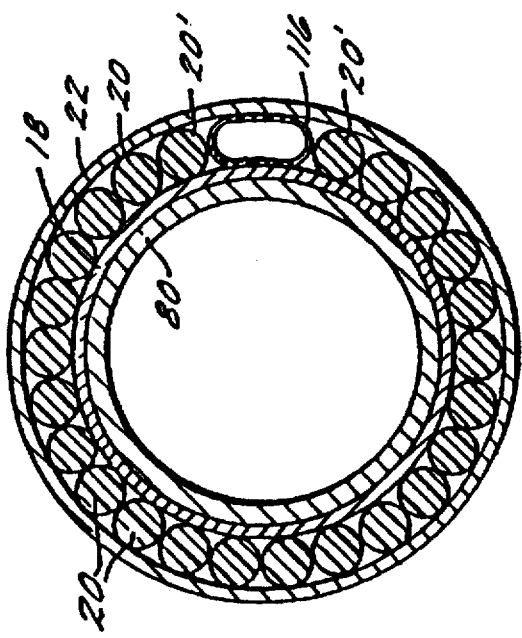
FIG. 8 is a cross-sectional elevation view along the line 8—8 of FIG. 1.

Referring first to FIG. 1, the optical viewing device of the present invention is shown generally at 10. Device 10 is comprised of three main sections including an objective lens section 12, a relay lens section 14 and and eye piece lens section 16. The particular embodiment of the present invention shown in FIG. 1 includes six lenses in the objective lens section 12, eighteen lenses in the relay lens section 14 and two lenses in the eye piece lens section 16 for a total of twenty-six lenses. For the most part, these lenses are spaced apart by air gaps and are retained in place by a series of spacer sleeves as will be discussed in more detail with regard to FIG. 5. Referring to FIGS. 1 and 8, the series of lenses and spacer sleeves are positioned within an inner tube 18. As will be discussed in more detail hereinafter, surrounding inner tube 18 is a plurality of optical fibers 20. Optical fibers 20 are sandwiched between inner tube 18 and an outer tube 22. Preferably, both inner tube 18 and outer tube 22 are comprised of a stainless steel. Both inner and outer tubes 18 and 22 terminate at a body housing 24 which houses a fiber optic connector 26 and a cleaning fluid injection port 28. In turn, body housing 24 includes an opening 30 for receiving an eye piece housing 32.

With reference now to FIGS. 1 and 2, the objective lens section 12 comprises six lenses including lenses 34, 36, 38, 40, 42 and 44. It will be appreciated that the physical and optical characteristics of each of the lenses 34-44 for objective lens section 12 (as well as relay lens section 14 and eye piece lens section 16) are set forth in Table 1. An aperture stop 45 (also shown in FIG. 4) abuts lens 36. Lenses 34 and aperture stop 45 are spaced apart from one another by a spacer sleeve 46. Similarly, lenses 38 and 40 are separated by a spacer sleeve 48. The gap 50 between lenses 34 and 36 and the gap 52 between lenses 38 and 40 each define an air space. Each lens 34, 36, 38, 40, 42 and 44 terminate along its circumferential periphery by a flanged portion. The size of the flanged portions are such so that all of the lenses have the same diameter even though the optical portions of the lenses may vary in size as indicated in FIG. 2. The flanged portions together with the spacer sleeves 46, 48 provide accurate and dimensionally correct spacing between the several lenses. Note that lenses 40 and 42 are in abutting relationship and are physically and optically interconnected by an optically clear acrylic cement. FIG. 2 depicts several light rays 54 which indicate how light reflected from an object to be viewed travels through objective lens section 12.

Each of the lenses 34-44 in objective lens section 12 (as well as the lenses in the eye piece and relay lens sections) are plastic and may be comprised of any suitable optical polymeric material, preferably polymethylmethacrylate, polystyrene and polycarbonate. In a preferred embodiment, the lenses 34-44 in objective lens section 12 (as well as selected other lenses in the relay lens section 14 and eye piece lens section 16) are comprised of different polymeric materials as indicated in Table 1.

Relay lens section 14 comprises eighteen lenses. These eighteen lenses are arranged in three repeating units, each repeating unit comprising two symmetrical sub-units of three unique lenses. One such repeating unit is shown in FIGS. 1 and 3 and identified at 54. As mentioned, repeating unit 54 includes two symmetrical sub-units 56 and 56'. In turn, each sub-unit 56, 56' each include three unique lenses 58, 60 and 62. It will be appreciated that the lens arrangement 56' is a mirror image of the lens arrangement 56.

In a manner similar to FIG. 2, representative light rays are shown at 64 and indicate the travel of said light rays through the relay lens section.

Symmetrically positioned at the center of relay section 14 is an aperture stop 66 (best shown in FIG. 4). Like aperture stop 45, aperture stop 66 comprises an annular disk and functions in a known manner to restrict light ray bundles from passing through the optical system.

Figure 5:
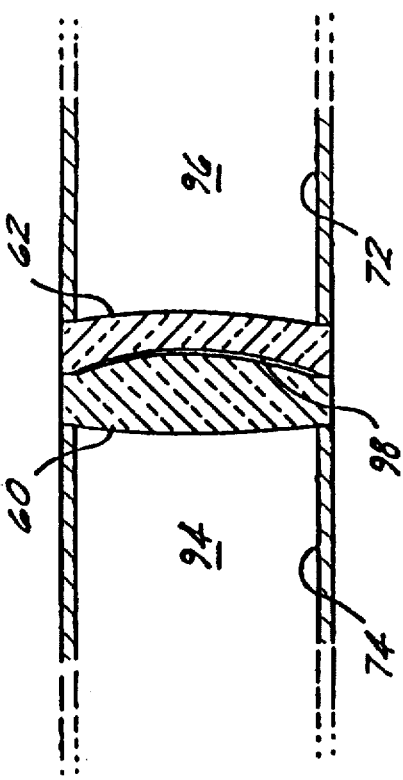
FIG. 5 is an enlarged side elevation view of a portion of FIG. 1 depicting a pair of spacer sleeves on either side of a pair of individual lenses in the relay lens section.

In a manner similar to objective lens section 12, the lenses 58, 60 and 62 are spaced from one another using a series of spacer sleeves (however it will be appreciated that lenses 60 and 62 abut one another via their respective outer flanges with a small air gap 98 resulting between the optical portions of lenses 60, 62 as best shown in FIG. 5). The lenses 58 and 60 are comprised of different polymeric materials as indicated in Table 1. Lenses 62 are comprised of glass (e.g., Glass F2 manufactured by Schott Glass Technologies, Inc.)

as indicated in Table 1. Glass lenses have a more homogeneous refractive index than that of commercially available injection molded plastic type lenses and, therefore, far less birefringence is induced in the light. This problem of induced birefringence was encountered with the plastic lenses 62 of U.S. Ser. No. 838,602, now abandoned, wherein most of the birefringence induced was induced by lenses 62 in the relay lens section due to their plastic composition. Accordingly, it is an important feature of the present invention that lenses 62 be comprises of glass. Relay lens section 14 includes thirteen spacer sleeves, namely sleeves 68, 70, 72, 74, 76, 78, 80, 82, 84, 86, 88, 90 and 92. FIG. 5 depicts an enlarged portion from FIG. 1 showing a pair of spacer sleeves 74 and 72 sandwiching therebetween lenses 60 and 62. As was discussed with regard to objective lens section 12, the lenses 60, 62 each have annular outer flanges which have the same diameter as do spacer sleeves 72, 74. It will be appreciated that the gap within the spacer sleeves between adjacent lenses is empty, and so may include air or any other desired gas (or vacuum). Also, as mentioned, a slight gap 98 exists between adjacent lenses 60, 62 with this gap 98 also including air or any other suitable gas. Both the spacer sleeves in relay section 14 and the spacer sleeves in relay section 12 are preferably comprised of a light weight aluminum material.

Figure 6:
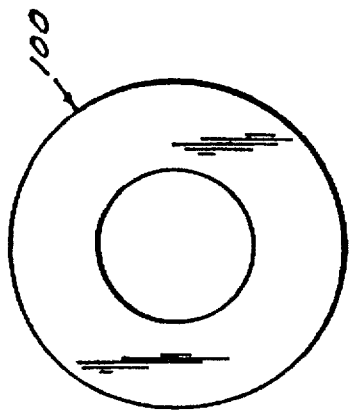
FIG. 6 is a front elevation view of a field stop positioned between the eye piece and relay lens sections of the optical viewing device of FIG. 1.
Figure 7:
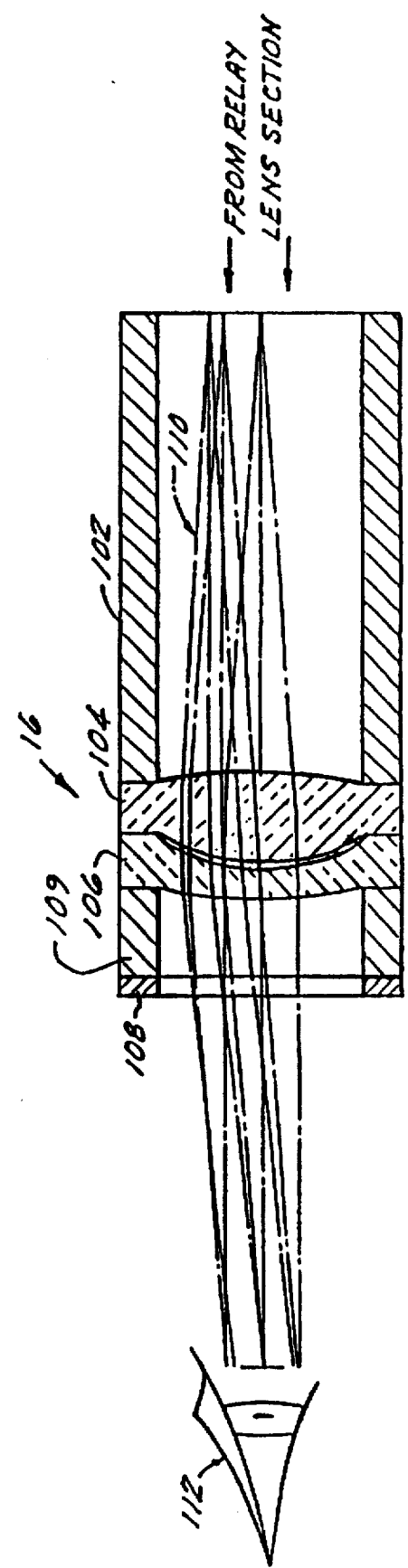
FIG. 7 is an enlarged cross-sectional elevation view of the eye piece section of the optical viewing device of FIG. 1.

Eye piece housing 32 houses the eye piece lens section 16 and a field stop 100 (see FIG. 6). Field stop 100 is preferably comprised of stainless steel and functions to define the field of view (FOV) of the optical system. The field stop is an annular disk and in one preferred embodiment has an outer diameter of 0.394" and an inner diameter of 0.167". Field stop 100 and eye piece lens section 16 is separated by a spacer sleeve 102 of the type described hereinabove with an air space residing within spacer sleeve 102. Eye piece lens section 16 comprises two lenses 104 and 106, each having outer flange sections which abut one another but provide a small air space therebetween. Lens 104 is comprised of a polymeric material as is indicated in Table 1. Lens 106 is comprised of glass (e.g., Glass F2 manufactured by Schott Glass Technology, Inc.) as indicated in Table 1. As discussed hereinabove, glass lenses induce far less birefringence than plastic lenses. This problem of induced birefringence was also encountered with the plastic lens 106 of U.S. Ser. No. 838,602, wherein most of the birefringence induced in the eye piece lens section 16 of U.S. Ser. No. 838,602 was induced by lens 106 of U.S. Ser. No. 838,602 due to its plastic construction. Accordingly, it is an important feature of the present invention that lens 106 be comprised of glass. The stop ring 108 and a small spacer sleeve 109 are used to retain lenses 104, 106 in proper position and orientation. As in the other spacings between the lenses, an air space is present between stop ring 108 and lens 106. Referring to FIG. 7, the light rays 110 are shown traveling from relay lens section 14 to eye piece section 16 and finally to the viewer's eye 112.

It will be appreciated that the total length of the combined objective lens and relay lens sections equals approximately 329 millimeters with twenty-four lenses, fifteen spacer sleeves and two aperture stops being utilized. It will further be appreciated that the number of lenses, spacers and aperture stops as well as the dimensions, are by way of example only, and that any number of lenses, spacer sleeves and dimensional relationships may be utilized depending on the particular length required for the optical viewing device desired and the end application thereof. The optical viewing device 10 shown in FIG. 1 along with the numbers of lenses, spacer sleeves and dimensional relationships finds particular utility in the medical field for use in an endoscope application.

Since the optical viewing device of the present invention is typically used to view remote locations which may have little or no illumination, the present invention includes a means for illuminating the remote end (the end to the right of the objective lens section) so that light from this illuminating means may be reflected from the object to be viewed and thereafter travel through device 10 as described above. In a preferred embodiment and with reference to FIGS. 8 and 9, the illuminating means comprises a plurality of optical fibers which are arranged in one or more layers along the outer circumference of inner tube 18. Optical fibers 20 are collected in a bundle in body housing 24 and attached to a commercially available and known fiber optic connector 26. In a known manner, a light source is positioned at the terminal end of connector 26 to provide light to fiber optic bundle 114. In this way, light is provided to the objective lens section for purposes of illumination.

Figure 9:
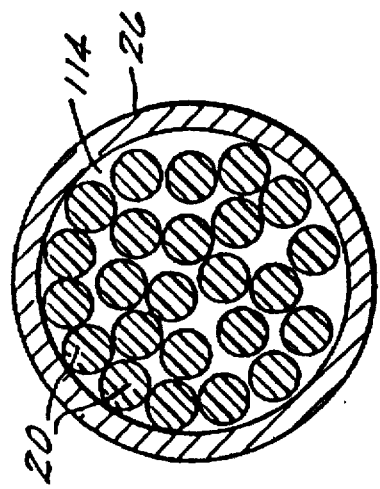
FIG. 9 is a cross-sectional elevation view along the line 9—9 of FIG. 1.
Figure 10:
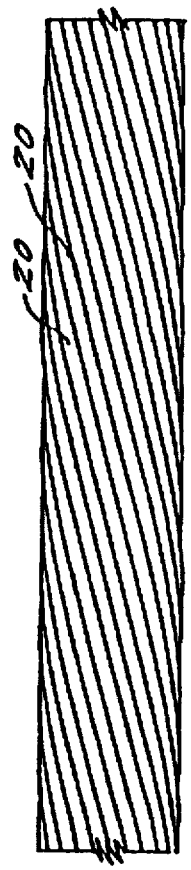
FIG. 10 is a side elevation view of a portion of the optical viewing device of FIG. 1 showing twisted illumination optical fibers.

In accordance with an important feature of the present invention, the optical fibers 20 are comprised of a suitable polymeric material such as acrylic or polycarbonate materials. The use of polymeric optical fibers is a significant feature of the present invention is as it is lower cost and more light weight relative to prior art glass fiber materials. However, one problem with polymeric optical fibers is that the field of illumination is relatively small (as compared to glass fibers) and may therefore not be as large as desired (which is typically a field of illumination at least equal to the FOV of the device 10). However, this problem has been overcome by an important feature of the present invention wherein the polymeric optical fibers 20 are twisted as shown in FIG. 10. Such twisting has been found to significantly increase the field of illumination to obtain a field of illumination which is equal to the desired field of view for the device 10. For example, it has been found that by twisting the fibers to an angle of 10.25 degrees, the field of illumination will cover 68°. It has also been found that by twisting the fibers to an angle of 16.66° the field of illumination will cover 80°. Preferably, the optical viewing device 10 of the present invention utilizes twenty-four one millimeter diameter acrylic fibers 20 as shown in FIGS. 8 and 9. Also, these fibers for the reasons mentioned above are twisted to an angle in the range of between 10° and 15°.

Housing body 24 (as well as eye piece housing 32) are preferably comprised of a molded plastic.

In certain applications, it may be desirable to provide a means for maintaining the outer surface of lens 34 (the first lens in objective lens section 12) clean and free of any obscurations. If such a cleaning means is desired, the present invention employs an optical port or valve 28 received in an appropriate opening in housing 24. Valve 28 is connected to a plastic tube 116 which runs longitudinally along the length of inner tube 18 and is sandwiched between a pair of optical fibers 20' as best shown in FIG. 8. Tube 116 terminates at end section 118 which protrudes outwardly from housings 18, 22 and is bent so as to be directed towards the outer surface of lens 34. Thus, when it is desired to clean lens 34, a suitable cleaning fluid is injected through valve 28, travels down through tube 116 and outwardly of tube end portion 118 where it impacts lens 34 thereby providing cleaning action.

The following Table 2 provides a number of optical parameters for an optical viewing device 10 in accordance with the present invention having the lens configurations, dimensions and respective spacings as set forth in Tables 1 and 2 above.

The present invention thus provides a relatively low cost and light weight optical viewing device which finds utility both as an endoscope and as a borescope and in any other application wherein a remote object positioned in cavity or the like must be viewed. The present invention is particularly low cost in that it utilizes, in a preferred embodiment, only eleven types of lenses (see Table 1) some of which are used in repetitive fashion for a total of only twenty-six lenses. Because nineteen of these lenses are molded from low cost polymeric materials and only seven of these lenses are comprised of glass, and because the prior art and relatively expensive glass rods are not used between the lenses, the present invention leads to both low cost and low weight. It will be appreciated that the cost of the viewing device of the present invention may be so low that in certain applications, the present invention may be a disposable item. The need for disposable viewing devices of the type described herein is particularly important in the medical field where infection and other contamination is an important consideration in medical instrumentation and therefore disposable devices are preferred.

What is claimed is:

1. An optical viewing device comprising:
   a tubular housing having opposed first and second ends with an eye piece section at said first end, an objective lens section at said second end and a relay lens section between said eye piece section and said objective lens section;
   said relay lens section comprising a plurality of rod-less lens groupings separated from each other by an open space, each of said lens groupings including two sub-groupings of symmetrically arranged plastic and glass lenses with at least some of said lenses being separated by gaps, at least one of said plastic lenses of said relays lens section being a positive lens.

2. The optical viewing device of claim 1 wherein at least one of said glass lenses of said relay lens section is a negative lens.

3. In an optical viewing device comprising a plurality of lenses disposed longitudinally within a tubular housing, the

TABLE 1

| LENSES | SURFACE | THICKNESS | RADIUS (mm) | CLEAR APERTURE | SPACER (mm) | MATERIAL | SECTION |
|---|---|---|---|---|---|---|---|
| 34 | 1 lens | .800 | 100,000 | 5.392 | | Acrylic | Objective |
| | 1 thickness | 7.001 | 5.534 | 5.392 | 6.284 | | |
| 36 | 1 lens | .800 | −57.879 | 2.711 | | Styrene | Objective |
| | 1 thickness | .167 | 6.870 | 2.711 | .043 | | |
| 38 | 1 lens | 2.000 | 44.355 | 2.045 | | Acrylic | Ojbective |
| | 1 thickness | .345 | −3.444 | 3.120 | .981 | | |
| 40 | 1 lens | 2.500 | 7.148 | 3.835 | | Acrylic | Objective |
| | 1 thickness | .000 | −3.127 | 3.835 | −.003 | | |
| 42 | 1 lens | 1.000 | −3.153 | 3.860 | | Styrene | Objective |
| | 1 thickness | .100 | 5.259 | 4.905 | .001 | | |
| 44 | 1 lens | 2.500 | 5.222 | 4.493 | | Acrylic | Objective |
| | 1 thickness | 8.435 | −4.925 | 4.883 | 8.445 | | |
| 58 | 6 lens | 1.500 | −6.252 | 5.500 | | Acrylic | Relay |
| | 6 thickness | 28.886 | −5.552 | 5.500 | 29.699 | | |
| 60 | 6 lens | 2.000 | 55.832 | 6.120 | | Acrylic | Relay |
| | 6 thickness | .109 | −7.289 | 6.120 | .000 | | |
| 62 | 6 lens | 1.000 | −7.361 | 6.605 | | Glass F2 | Relay |
| | 6 thickness | 14.721 | −17.468 | 6.985 | 15.074 | | |
| 104 | 1 lens | 2.500 | 10.741 | 6.300 | | Acrylic | Eye Piece |
| | 1 thickness | .102 | −5.682 | 6.300 | −.001 | | |
| 106 | 1 lens | 1.000 | −5.605 | 6.550 | | Glass F2 | Eye Piece |
| | 1 thickness | | −20.087 | 10 | | | |
| Spacer | 2 thickness | 7.026 | | | | | |

TABLE 2

| Field of View | 68° |
|---|---|
| Apparent Field of View | 12.8° |
| Exit Pupil Diameter (mm) | 2.90 |
| Optical Invariant | 0.146 |
| Illumination Trans. | 60–80% |
| Bulk Image Transmission | 60–70% |
| Relative Transmission | 0.013–0.015 |
| Vignetting @ Edge of the Field | 30% |
| MTF @6 cycles/deg (70% Field) | 0.8 |
| Distortion | 20% |
| Relative Aperture | F/7 |
| Entrance Pupil (mm) | 0.56 |
| Working Distance (mm) | 300 |

While preferred embodiments have been shown and described, various modifications and substitutions may be made thereto without departing from the spirit and scope of the invention. Accordingly, it is to be understood that the present invention has been described by way of illustrations and not limitation.

lenses being grouped and defining an eye piece section, relay lens section and objective lens section, the improvement comprising:
   said lenses in said relay lens section arranged in groups, each group including two sub-groupings of symmetrically arranged plastic and glass lenses with at least some of said lenses being separated by gaps.

4. The optical viewing device of claim 3 wherein at least one of said plastic lenses of said relay lens section is a positive lens and wherein at least one of said glass lenses of said relay lens section is a negative lens.

5. The optical viewing device of claim 4 wherein said relay lens section is devoid of rod lenses.

6. An optical system for an endoscope, which comprises:
   an objective lens system;
   a relay lens system, the relay lens system including a plurality of lens groupings separated from each other by open space, each lens grouping arranged in two subgroupings of symmetrically arranged lenses, each subgrouping having at least one positive lens made from an optical polymeric material and at least one negative lens made from an optical glass; and an eye lens system.

7. The optical system according to claim 6 wherein the relay lens system includes three lens groupings.

8. The optical system according to claim 6 wherein each lens subgrouping has three lenses.

9. The optical system according to claim 8 wherein each subgrouping consists of a first single curved lens and a first doublet lens and wherein the doublet lens includes a first lens fabricated from an optical polymeric material and a second lens fabricated from an optical glass.

10. The optical system according to claim 6 wherein at least one of the lenses is a positive lens comprising the polymeric material and wherein at least one of the lenses is a negative lens comprising the optical glass.

11. An optical viewing device, which comprises:

a) a frame portion;

b) an elongated portion extending from the frame portion, the elongated portion including:
an outer tube; and
an inner lens tube disposed within the outer tube;

c) a plurality of optical fibers circumferentially disposed within a space defined between the inner and outer tubes for providing illuminating light; and d) an optical system at least partially disposed within the inner lens tube for transferring an image of an object, the optical system including:
 i) an objective lens arrangement for forming an image of an object;
 ii) a relay lens arrangement for transferring the image through the elongated portion, the relay lens arrangement including a plurality of lens groupings, each lens grouping arranged in two subgroupings of symmetrically arranged lenses, each subgrouping having at least one lens comprising an optical polymeric material and at least one lens comprising an optical glass; and
 iii) an eye lens arrangement for viewing the image transferred by the relay lens arrangement.

12. The optical viewing device according to claim 11 wherein the relay lens arrangement includes a positive lens fabricated from a polymeric material and a negative lens fabricated from an optical glass.

* * * * *